United States Patent [19]

Butland

[11] Patent Number: 5,194,289

[45] Date of Patent: Mar. 16, 1993

[54] METHOD FOR LABELING AN OBJECT FOR ITS VERIFICATION

[75] Inventor: Charles L. Butland, Playa del Rey, Calif.

[73] Assignee: Butland Trust Organization, Los Angeles, Calif.

[21] Appl. No.: 597,859

[22] Filed: Oct. 15, 1990

Related U.S. Application Data

[63] Continuation-in-part of Ser. No. 263,058, Oct. 27, 1988, abandoned, which is a continuation-in-part of Ser. No. 868,955, May 30, 1986, Pat. No. 4,882,195, which is a continuation-in-part of Ser. No. 857,929, Apr. 30, 1986, abandoned.

[51] Int. Cl.$^5$ .................. B05D 5/00; A61B 5/117
[52] U.S. Cl. .................. 427/1; 427/7; 427/145; 427/160
[58] Field of Search .................. 427/1, 7, 255.6, 145, 427/160

[56] References Cited

U.S. PATENT DOCUMENTS

| | | | |
|---|---|---|---|
| 1,374,208 | 4/1921 | Jones | 427/7 |
| 2,066,535 | 1/1937 | Lucas | 427/7 |

FOREIGN PATENT DOCUMENTS

| | | | |
|---|---|---|---|
| 2551814 | 5/1977 | Fed. Rep. of Germany | 427/7 |
| 3151012 | 7/1983 | Fed. Rep. of Germany | 427/7 |
| 1456784 | 10/1966 | France | 427/7 |

*Primary Examiner*—Janyce Bell
*Attorney, Agent, or Firm*—Mueller and Smith

[57] ABSTRACT

Disclosed is a method for labeling an object for its identification. The method comprises applying a selected person's fingerprint to said object at a predetermined location upon said object. Next, the predetermined location is exposed to a vaporous agent comprising vapors of a cyanoacrylate ester. The selected person's fingerprint or said vapors of a cyanoacrylate ester. The selected person's fingerprint or said vapors of cyanoacrylate ester bear a detectable amount of an ultra-violet radiation sensitive dye. Exposing the predetermined location to said vapors create a permanent impression of the fingerprint on the object which impression is perceptible only in the presence of UV radiation. Prime objects for identification in accordance with the method of the present invention include works of art, negotiable instruments, credit card receipts, and like objects.

6 Claims, No Drawings

METHOD FOR LABELING AN OBJECT FOR ITS VERIFICATION

CROSS-REFERENCE TO RELATED APPLICATIONS

This application is a continuation-in-part of U.S. application Ser. No. 07/263,058, filed Oct. 27, 1988, now abandoned which in turn is a continuation-in-part of U.S. application Ser. No. 868,955, filed May 30, 1986, now U.S. Pat. No. 4,882,195 which in turn is a continuation-in-part of U.S. application Ser. No. 857,929, filed Apr. 30, 1986, now abandoned, the disclosures of which are expressly incorporated herein by reference.

BACKGROUND OF THE INVENTION

The present invention relates to the labeling of objects for verifying authenticity and me particularly to the use of a selectedly-perceptible mark, such as a fingerprint, therefor.

Many objects require verification for authenticity. Such objects include paintings, sculptures, and like works of art; video cassette recorders, televisions, and like household objects; computers; printers, and like office and business equipment; packages in which valuable objects need to be authenticated and documented so that the owner knows that they are genuine. This same knowledge also is required by an insurance company prior to insuring a work of art. With respect to the authentication and documentation of works of art, for example, a detailed and exhaustive undertaking is required to be conducted by a recognized and bonded expert. This procedure includes physical authentication utilizing detection methods involving the use of infrared spectroscopy, X-ray radiography, ultra-violet spectroscopy, raking light procedures, pigment analysis, and like procedures. For a lithograph, for example, the lithograph must be unframed and free of obstacles for inspection. A careful scrutiny of the entire print back and front surface must be undertaken in order to detect evidence of variations from perfection including tears or folds, bacterial action, smudges, handprints, dirt, stains and like imperfections, which originate both from the original printing and from later abrasion thereof. Observation additionally must extend to the kind of base material used, total count of colors and variations, and other variations from normal. It will be observed that a qualified expert can undertake such an examination.

Next, the historical information of the work of art must be considered. For a painting, for example, the history of the painting must be recorded and verified. This history includes where the painting came from, the date of origin of the painting, all sales records and auction records of the painting, diaries of the painting, and specific collector or museum documentation which accompanies the painting.

Now, such procedure for authentication of works of art ordinarily is required when the work of art is insured, when the art changes ownership, and even when the work of art is placed on loan and then returned. It will be observed that the recommended authentication procedure involves much time and expense. Nevertheless, museums, owners of works of art, insurance companies, and like interested parties must insist on such authentication procedures for their own protection.

Other instances of identification include the ability to verify ownership of more common objects such as household appliances, business equipment, and like objects. Often, these objects have no serial number or other unique means of identification, or the number can be removed easily following a theft. Thus, a simple method for reliably identifying such objects would be welcomed by the owners.

Still another field which requires verification of ownership involves credit cards and checks, for example. Credit card theft amounts to millions of dollars annually, yet detection of the unauthorized use use of a credit card often is difficult or inconvenient for the store owner. The same holds true for negotiable instruments like checks. Thus, there is a substantial need for providing either a deterrent against those who would improperly or illegally utilize credit cards or stolen checks, or for the apprehension of such individuals following such unauthorized or illegal use.

BROAD STATEMENT OF THE INVENTION

The present invention is addressed to providing a simple, yet reliable method for labeling an object for its verification. Broadly, the method of the present invention for leveling an object for its verification comprises applying to a predetermined location on said object, a mark which creates a permanent impression thereof which is perceptible only in the presence of ultra-violet (UV) radiation. One embodiment of the present invention comprises applying a selected person's fingerprint to the object at a predetermined location upon said object. Next, the pre-determined location is exposed to a vaporous agent comprising vapors of a cyanoacrylate ester. Either the fingerprint or the cyanoacrylate ester bears a detectable amount of an agent. The vaporous agent creates a permanent impression of the fingerprint on the object, which impression is imperceptible only to in the presence of selected wavelengths of energy by virtue of said agent. Desirably, the agent is an ultra-violet radiation sensitive compound or dye which is not visually perceptible except upon application of ultra-violet (UV) radiation to the predetermined location.

Alternatively, a substrate can be prepared to contain a binder which bears the UV sensitive agent. The substrate can be a pad bearing a reservoir of the binder/UV agent or can be a tape having a transferrable film of the binder/UV agent. Next, a marker or an imprinter, such as a selected person's finger, is contacted with the substrate. Finally, the contacted finger is applied to the object at a predetermined location thereupon to crate a permanent impression of the fingerprint on the object, which impression is perceptible only in the presence of UV radiation. For all embodiments of the invention, a clear plastic laminate, for example, optionally, can overlay the fingerprint location on the object.

As an augmentation to the UV determination of the permanent impression, amino acids or protein fragments derived from the hair of a selected individual, e.g. an artist for his painting, can be incorporated into the formulation of binder and UV sensitive agent. A comparison of such amino acid or protein fragments of a suspected stolen object then could be made with a retained sample and authentication verified.

Advantageously, the object can be a work of art, such as painting or a sculpture. Alternatively, the object may be a credit card receipt or voucher utilized at the time that the credit card is used in making a purchase. At such point of purchase, the object also may be a negotiable instrument such as a check. In the latter two cases, the object is being identified, but more importantly, perhaps so is the person utilizing the credit card or the check. Under such circumstances, the method of the present invention may become an effective deterrent against the unauthorized use of credit cards and checks, which forms another aspect of the present invention.

Advantages of the present invention include a simple, yet reliable means for labeling objects for identification. Another advantage is that the label is not perceptible to people absent the application of appropriate wavelengths of energy such as UV radiation. Another advantage is that the label can last for an almost indefinite period of time. These and other advantages will become readily apparent to those skilled in the art based upon the disclosure contained herein.

DETAILED DESCRIPTION OF THE INVENTION

Once an object is identified and verified, it can be labeled in accordance with the inventive technique disclosed herein so that its authentication at a later data is enhanced materially. Based upon the foregoing description in the field of art verification, it can be appreciated that art owners, insurance companies, and art experts can use all the assistance which can be provided for them in properly identifying and verifying the authenticity of works of art. The present invention provides such assistance by providing an "invisible" label, the location of which on the object is not published and is not apparent to the naked eye. Only upon the application of selected wavelengths of energy at the right location on the object is the fingerprint label perceptible. Paintings and sculptures, for example, can be identified and authenticated initially with the authentication procedure involving the application of a fingerprint thereto. At a later date when the work of art needs to be authenticated again, not only can the owner utilize the services of an art expert in conjunction with the historical paperwork on the art, but the observance of the fingerprint label will provide further evidence as to the genuineness of the work of art being evaluated. That is, when a museum loans a work of art, it will know that the work of art being returned is the same work of art that was lent in the first instance.

By properly preserving the secrecy of the fingerprint labeling procedure, the value of the fingerprint label is enhanced. That is, the location of the fingerprint label can be controlled as well as whose fingerprint is applied thereto. In fact, combinations of fingerprints can be utilized at the same or at different locations on the object for providing further fool-proof means for labeling the object. Since Dactyloscopy is a recognized science by the courts, recognized experts for reading fingerprints can be utilized for verifying the authenticity of the fingerprint labels. As noted above, the fingerprint labeling technique of the present invention can be utilized on any object. Objects as common-place as television sets, video cassette recorders, and the like can be identified by the fingerprint label technique of present invention. Should such objects be stolen, the criminal would not be able to mask the identity of the object by removing serial numbers applied by the manufacturer. Indeed, the fingerprint label could be located at almost any surface of the object so that its identity would be firmly established.

One useful technique for implementing the present invention involves the application the fingerprint label to an object as described herein. Next, a fluorescent light would be shined upon the surface whereat the fingerprint is located and a record, e.g. photograph, of such surface and fingerprint label taken. The photograph would document the exact placement location of the fingerprint label. The photograph could be maintained within the files of the company offering such fingerprint labeling service. The likelihood of a fingerprint being placed in the same location is remote, so that the fingerprint labeling technique of the present invention is a near-foolproof technique for labeling objects for their identification and verification. It will be appreciated that when the UV light is turned off, the "invisible" mark again becomes invisible to the observer. The mark can be rendered visible numerous times without affecting it or its ability to remain invisible in the absence of the UV light.

Moreover, the present invention can be implemented to even a further degree of sophistication utilizing the new breed of "high tech" fingerprint computer equipment which currently is being put into service by some law enforcement agencies. This aspect of the invention involves the maintenance of a duplicate copy of the fingerprint label applied to the object either on a card which the owner of the object retains or company offering such fingerprint labeling service retains it. If the labeled object were stolen and recovered, or its authenticity questioned, the fingerprint could be indentified. By cross-referencing the identified fingerprint, the object, e.g. a piece of art, actually could be identified and the true owner determined. This technique could be done through the use of a single fingerprint classification and identification system that currently exists within the law enforcement arena. Besides manual matching of fingerprints, the use of fingerprint computer equipment also could be implemented.

Another field which will benefit greatly by the fingerprint labeling technique of the present invention in the credit card and negotiable instrument field. Often, credit cards and checks (e.g. a negotiable instrument) are stolen and improperly used. At the point of sale, the sales clerk need only require the presenter of the credit card or check to place a fingerprint upon a surface of the credit card receipt or voucher, or upon the negotiable instrument itself, followed by exposure thereto cyanoacrylate vapors, in order to be able to authenticate the credit card purchase or negotiable instrument being presented for payment. It is not likely that credit card or check thieves would be so ready to have their fingerprint permanently attached to the credit card receipt or check which leaves their possession and may eventually be presented to the police should the transaction be improper. Thus, the fingerprint labeling technique of the present invention should prove to be a deterrent against the unauthorized use of credit cards and of stolen checks.

A further field which will benefit greatly by the fingerprint labeling technique of the present invention is the travel field, particularly with respect to the use of passports and visas by international travelers. The use of forged or false passports is an ever-increasing problem which customs officials at various international airports must deal with on a daily basis. Besides matching the physical description on the passport to the bearer thereof and the attempted verification of the genuineness of the passport, the fingerprint labeling technique of the present invention also could be utilized. Again, the passport would bear the non-removably and "invisible" fingerprint of the true bearer which could be accomplished at the issuance of the passport. Thereafter, the fingerprint of the bearer could be matched to the fingerprint on the passport should questions as to the authenticity of the passport be raised upon its presentation. An advantage in using the fingerprint label of the present invention is the near-impossibility of removing the fingerprint from the face of the passport once it has been applied. While use of solvents or etching techniques may result in removal of the fingerprint, likely destruction of the surface of the passport would occur also. Such alteration, then would be detectable by the customs agent inspecting the passport. Thus, an effective technique for aiding customs officials in verifying the authenticity of passports is yet another advantage of the present invention.

Three techniques for practicing the present invention can be envisioned readily. Two of the techniques involve the fuming of the object for its labeling. One embodiment involves the use of a pad which bears the UV dye along and wherein the fuming agent comprises the cyanoacrylate or other binder. The second fuming technique involves the application of the fingerprint to the object to be labeled followed by the fuming with the binder and dye combination. The third technique involves a pad which contains both the binder and the UV dye, which pad is contacted by the finger and thereupon the fingerprint transferred to the object being labeled. When speaking of "fingerprint", such fingerprint usage is preferred since it is unique for each individual and is a convenient manner for marking objects to be labeled for verification. In a broader sense, the "label" applied to the object need only be a mark which creates a permanent impression thereof which is preceptible only in the presence of UV radiation. When a pad bears both the binder and UV dye, then any convenient stamp or similar imprinting implement can be utilized to apply a variety of forms of marks including a digitized code for fingerprints, a person's Social Security or drivers license number, a person's birthday, or any other series of numbers. For that matter, designs and logos can be applied as a mark for creating a permanent impression thereof which is preceptible only in the presence of UV radiation. The invention will be described with particularity for utilizing fingerprints as the invisible mark applied for labeling an object, though such description is by way of illustration and not limitation of the present invention.

The fuming embodiments of the present invention most readily are associated with alpha-cyanoacrylate binders, though other thermoplastic or thermoset binders possibly could be adapted to such fuming technique. In the field of Dactyloscopy, latent fingerprints have been developed with cyanoacrylate esters as proposed in, for example, U.S. Pat. Nos. 3,523,628, 3,678,014, 4,103,081, 4,297,383, 4,407,842, and 4,461,235. In fact, a much improved cyanoacrylate ester aerosol spray method is disclosed in commonly-assigned application Ser. No. 849,380, filed Apr. 8, 1986. These proposals operate upon the apparent attraction of cyanoacrylate esters for amino acids and riboflavins secreted through the human skin and present in latex fingerprints. The result of the contact of vapors of cyanoacrylate with the latent fingerprint is a physical impression of the fingerprint that can be conventionally "lifted" by law enforcement personnel utilizing carbon dust, magnetic powder, talc, or the like techniques. Location of the fingerprints often is assisted by inclusion of a UV dye in the cyanoacrylate vapors which causes the developed latent fingerprints to fluoresce under the influence of UV radiation. Common in these prior proposals is the use of cyanoacrylate ester vapors for the detection of latent fingerprints so that the individual leaving the latent fingerprints can be identified. Most certainly this use of latent fingerprints detection is associated with crime and the apprehension of criminals. The present invention is unique in its adaptation of cyanoacrylate development of latent fingerprints to uses far afield from the identification of criminals through the use of latent fingerprints. Indeed, the method of the present invention involves the application of such cyanoacrylate latent fingerprint technology to the labeling of objects for verifying their authenticity.

As noted above, several prior proposals deal with the cyanoacrylate development of latent fingerprints. While any of those techniques can be used for implementation of the present invention, preferably, the cyanoacrylate ester aerosol spray method of Ser. No. 849,380 is utilized. The utilization of an aerosol container of cyanoacrylate ester has many advantages with respect to the application of the cyanoacrylate vapors to an object being fumed for the fixation of a fingerprint label. It may be desirable to include a UV dye in the cyanoacrylate ester itself as proposed in said co-pending application. Alternatively, for works of art, it may be preferred that the finger or thumb of the person whose print is being affixed to the object be contacted with a pad or cloth containing the UV dye so that the latent fingerprint applied to the object, rather than the cyanoacrylate ester itself, contains the UV dye. The exposure of such a UV-impregnated fingerprint to vapors of cyanoacrylate ester still ersult in a fixed, permanent fingerprint which fluoresces in the presence of UV radiation. Also, this embodiment of the present invention does not expose sensitive areas of the object to air-borne UV dye which may damage the work of art itself.

Alkyl esters of alpha-cyanoacrylates are known in the art. Typically, the alkyl ester group will be a $C_1$-$C_6$ group, and preferably a $C_1$-$C_3$ alkyl group (e.g. a mixture of methoxyethyl cyanoacrylate and ethoxyethyl cyanoacrylate). In utilizing the preferred aerosol spray method, a halogenated organic solvent is included in the container which solvent is inert with respect to the cyanoacrylate, has a low boiling point (e.g. about 167° F.) and desirably is non-flammable for safety purposes. Halogenated organic solvents which meet this diverse criteria include, for example, the low-boiling point chlorinated hydrocarbons or fluorocarbons, chloro-fluorocarbons, or mixtures thereof. These solvents additionally should not be deleterious to or damage the objects being exposed to the cyanoacrylate vapors. Preferred halogenated organic solvents are di-chloro fluoromethane, di-chloro tetra-fluoroethane, tri-chloroethane, tri-chloro fluoromethane, and the like and mixtures thereof. The cyanoacrylate ester spray method utilizes the mixture of cyanoacrylate and halogenated organic solvent which normally ranges from between about 1 and 99 percent by weight cyanoacrylate and advantageously this proportion is between about 1 and 10 percent by weight. The concentration the mixture in the organic propellant often ranges from between about 50 to 60 percent by weight. The cyanoacrylate proportion, of course, can vary depending upon the type of cyanoacrylate, type of solvent, type of propellant, pressure of the contents in the container, orifice size, and like factors taught in the cited copending application. Preferred propellants are from the methane gas series and include, for example, ethane, propane, butane, pentane, and their halogenated derivatives (e.g. mono-fluoroethane, mono-chloroethane, etc.) and the like and even mixtures thereof.

While the object to be fumed can be placed in a small room or like confined area for exposure to the cyanoacrylate ester vapors, preferably, a vapor tank specially constructed for such purpose is utilized. Such tanks have been proposed in the art. The preferred such tank is disclosed in commonly-assigned U.S. Pat. No. 4,700,657. Such vapor tank, or a smaller or larger version thereof, advantageously can be utilized with the fingerprint labeling technique of the present invention. For credit card receipts and checks, for example, a smaller version which can be utilized at the point of sale in various stores is used to fume such small objects at the time the sale is made. The preferred vapor tank utilizes the preferred aerosol spray method which makes the fingerprint labeling operation extremely simple to utilize at the time that the sale is being made. In fact, only a matter of seconds or minutes are involved in the fixation of the applied fingerprint to the object. Should the person presenting the credit card or check refuse to have the fingerprint fixed, the sales clerk would be immediately alerted to the possibility of an anauthorized use taking place. The credit card or check can be confiscated immediately and appropriate security personnel notified.

While the cyanoacrylate fuming procedure described above is quite efficacious, on some occasions, it would be more convenient to adapt such fuming system to eliminate the fuming, yet still achieve transfer of the invisible fingerprint to the object to be labeled. A convenient method for accomplishing this involves the contact of the person's finger with a pad which bears the UV dye, which finger can then be contacted at the predetermined location on the object. For permanence in accordance with the present invention, the pad would bear the cyanoacrylate dissolved in a solvent along with the UV dye. While such embodiment is functional, the reactivity of the cyanoacrylate ester minimizes the convenience of this alternative procedure. Accordingly, when it is desired to use a pad bearing the UV dye, yet retain the invisible and permanence aspects of the present invention, the pad should contain a binder which bears the UV sensitive dye. Appropriate binders comprise hardenable materials, including, for example, thermoplastic resins. Thermoset resins, and penetrating carriers effective in establishing chemical and/or physical association of the UV dye with the surface of the object being labeled. Thermoplastic resins include, for example, polyesters, urethanes, acrylics, ethylene vinyl acetate copolymers, vinyl chloride homopolymers and copolymers, styrene butadiene polymers, styrene acrylonitrile polymers, silicone resins, cellulosic resins, ionomers, and the like and mixtures thereof. Thermosetting materials include, for example, air drying polyesters, urethane-forming resins formulated from polyols and polyisocyanates, conventional two-component epoxy resins with conventional hardeners (e.g. polyamine resins), UV curable resins, moisture-curable urethane resins, enzyme-curable resins, electron beam curable resins, radio-frequency curable resins, and the like, and mixtures thereof. So long as the binder, optionally with a solvent, can retain the UV dye, and provide permanence to the fingerprint on the object being labeled, such binder is suitable for use in accordance with the precepts of the present invention.

For present purposes, "permanent" as applied to the fingerprint label on the object means that the fingerprint is incapable of being removed from the object in the ordinary course of intended handling and usage of the object for a time adequate for identification and/or verification of the object to occur. For some objects, it may be desirable that the fingerprint label remain affixed to the object and identifiable in presence of UV radiation for many years. Such objects would include works of art, household appliances, machinery, automobiles, automobile parts, and the like. Some objects, however, require identification and/or verification only for a limited period of time. Credit card receipts would be one such example wherein a limited time period would apply. In this regard, once the purchase has been confirmed by the holder of the credit card, for example, the validated transaction no longer requires that the paper copy of the credit card receipt retain the fingerprint label. Thus, such a label need only be "permanent" for a limited period of time, say several weeks to several months.

Continuing with the description of thermoplastic and thermoset resins, specific examples include, for example, latex copolymers including methyl methacrylate/ethyl acrylate copolymers, styrene/butyl acrylate copolymers, styrene/butadiene copolymers, styrene/butyl acrylate/methacrylic acid/acrylic acid copolymers, methyl methacrylate/methacrylic acid/ethyl acrylate copolymers, methacrylic acid/butadiene/styrene copolymers, methyl methacrylate/butyl acrylate copolymers, butadiene/methacrylic acid copolymers, butadiene/acrylonitrile/methacrylic acid copolymers, butadiene/acrylonitrile/methacrylic acid copolymers, methacrylic acid/methyl methacrylate/ethyl acrylate/acrylic acid/ethyl acrylate copolymers; tongue oil/fumeric acid/pentaerythritol copolymers, and the like and mixtures thereof. Thus, it will be observed that a wide variety of thermoplastic and thermoset materials are suitable for use in accordance with the precepts of the present invention.

Penetrating carriers which are effective in establishing chemical and/or physical association of the UV dye with the surface of the object being labeled may be termed as solvents, which optionally may be reactive, e.g. UV curable acrylic monomers. Alternatively, for some substrates, such as paper or plastic, a vegetable oil or other carrier may be effective in penetrating into the substrate and carry the UV dye along with it. Whether the vegetable oil or other solvent remains or evaporates does no matter so long as the UV dye in the form of the fingerprint remains firmly established or permanent for the requisite time appropriate for the object being labeled. Of course, the label also should not be readily perceptible to the human eye without the aid of UV radiation. Finally, magnetizable particles can be applied to the formulation and the permanently applied mark detected thereby, e.g. using a U.S. Bank Notes IC Detector, No. 1175N (John Manufacturing Ltd.; Kawloon, Hong Kong).

The substrate which bears the binder/UV sensitive agent combination can be a simple porcelain, rubber, fabric, or like pad which retains the material therein. Alternatively, a quite unique embodiment of the present invention involves the formation of a film of the binder/UV dye combination which is drawn down on a film, e.g. a cellulosic film or polymeric film such as a polyethylene terephthalate film (marketed under the trademark Mylar, E.I. Du Pont de Nemours and Company). A second, release film then is overlaid the film in conventional fashion. The thus-formed laminate structure can be in the form of a roll of tape for convenient usage of it. When the transfer of the fingerprint is desired, the tape need only be unrolled and an appropriate amount cut off. The two substrates then are parted to leave exposed one of the substrates which still bears a film of the binder/UV agent combination. A person then need only contact such film with a finger or thumb and then apply the contacted finger or thumb to the object being labeled. The spent substrate then conveniently can be disposed in an appropriate receptacle. A convenient, inexpensive, and disposable fingerprint identification system has been revealed.

Fluorescent dyes which may be utilized in the container bearing the cyanoacrylate ester or which may be contained in a gauze or pad impregnated therewith, include those fluorescent dyes conventionally proposed in the art in the latent fingerprint detection field. These fluorescent dyes include, for example, various rhodamines, such as Columbia Blue, 8-hydroxy-1,3,6-pyrene-trisulfonic acid trisodium salt (HOPSA, Eastman Chemical Company), Rhodamine B, or Hostacell yellow 8G (American Hoechst Corporation). The ultra-violet source exposes the fingerprint labels when shined on the object at the appropriate location where the fingerprint label is located.

As a further and/or alternative means of identification, especially when an artist is involved, involves cutting a lock of hair from the artist, digesting it with appropriate enzymes or chemicals to produce either free amino acids, protein fragments, or combinations thereof, and incorporate this "soup" into the marking fluid disclosed herein. Detection, then, would involve dissolving the marking fluid from the suspected forgery, purifying it for high pressure liquid chromatography (HPLC) analysis, separating the amino acids or protein fragments (if any) on a chromatographic column, and then comparing it to a reference standard prepared from the artist from his hair. The mark is "permanent" as described herein, can be located by virtue of the presence of the UV agent which provides one means for identification, followed by the amino acid/protein fragment comparison that would unquestionably authenticate the object.

It will be observed that the present invention has apparent utility in a wide variety of fields beyond those described herein. The disclosure herein illustrates the presently-known preferred embodiments for utilizing the fingerprint labeling technique of the present invention. It will be readily apparent to those skilled in the art that a wide variety of other objects may be suitably labeled in accordance with the precepts of the present invention for their identification. Such additional objects and circumstances are included within the scope of the present invention in accordance with the precepts thereof. All citations cited herein are incorporated expressly herein by reference. The following examples show how the present invention has been practices but should not be construed as limiting.

EXAMPLES

Example

An acrylic latex (43 parts styrene/45 parts ethyl acrylate/12 parts hydroxy ethyl acrylate) at 50% solids in water was mixed with a UV fluorescent dye (fluorescein) and poured onto a sponge contained in a glass dish. Touching the sponge with the finger of one's hand followed by application of the finger to metal, glass, or wood resulted in the reproduction of a polymer film structure which was an exact replication of the fingerprint of the person who contacted the sponge. Upon drying of the polymer film (evaporation of the solvent), a rigid and durable (good adhesion) fingerprint structure formed. This fingerprint structure was not visible to the unaided eye, though was readily perceptible when a UV light source was shined upon it.

Example 2

The same acrylic latex/dye system of Example 1 was applied as a thin film between two sheets of Mylar material (Mylar brand polyethylene terephthalate film, E.I. Du Pont de Nemours and Company). This laminate structure was stable for several months in that the film remained soft and pliable during the storage time period. Removal of the top Mylar film structure exposed the latex/dye film layer which then was contacted with a person's finger to effect film transfer. The person's finger then retransferred the latex/dye material to several solid objects, including metal, glass, and wood. This second transfer process replicated the fingerprint which became durable or permanent upon exposure to air, yet was invisible to the naked eye absent the presence of UV light.

Example 3

The formulation comprised a methylmethacrylate-based acrylic latex (Rhoplex AC-64, 60–61% solids, pH 9–9.5, viscosity 600 cps, density 8.8–8.9 lb/gal, sp. gr. 1.06 g/cc, Rohm and Haas Co.) containing Columbia Blue or HOPSA fluorescing agents (about 0.2 wt-%). Both formulations dried to non-visible marks with fingerprints and a conventional office-type stamp on paper, wood, and other surfaces. The mark became visible under a U.V. light source. Another suitable resin system used was P & L 38/Statin H17 formulation (a soya-based alkyd, Pratt and Lambert Paint Co.).

I claim:

1. Method for labeling an object for identification which comprises the steps of:
   (a) preparing a substrate to contain a binder bearing an ultra-violet (UV) radiation sensitive dye and an amino acid or protein fragment from the hair of an individual;
   (b) contacting a marker with said substrate; and
   (c) applying said contacted marker to an object at a location thereupon to create a permanent impression on said object, which impression is perceptible only in the presence of UV radiation.

2. The method of claim 1 wherein said marker comprises a person's finger.

3. The method of claim 1 wherein said binder comprises a thermoplastic resin or thermoset resin.

4. The method of claim 3 wherein said thermoplastic resin or thermoset resin is selected from the group consisting of a polyester, a polyurethane, an acrylic resin, an ethylene vinyl acetate copolymer, a vinyl chloride homopolymer or copolymer, a styrene butadiene polymer, a styrene acrylonitrile polymer, a silicone resin, a cellulosic resin, an ionomer, an air-drying polyester, an epoxy resin, and mixtures thereof.

5. The method of claim 1 wherein said binder comprises a carrier effective in establishing one or more of chemical or physical association of said ultra-violet radiation sensitive dye with said object.

6. The method of claim 5 wherein said carrier comprises a vegetable oil.

* * * * *